United States Patent [19]

Samejima et al.

[11] 4,218,333
[45] Aug. 19, 1980

[54] PROCESS FOR THE PREPARATION OF PHARMACEUTICAL SUBSTANCE-CONTAINING MICROCAPSULES

[75] Inventors: Masayoshi Samejima, Minoh; Goichi Hirata, Hirakata, both of Japan

[73] Assignee: Tanabe Seiyaku Co., Ltd., Osaka, Japan

[21] Appl. No.: 929,224

[22] Filed: Jul. 31, 1978

[30] Foreign Application Priority Data

Aug. 11, 1977 [JP] Japan ................... 52-96749

[51] Int. Cl.$^2$ .............................. B01J 13/02
[52] U.S. Cl. ................... 252/316; 424/19; 424/35; 424/258; 424/263; 424/280
[58] Field of Search ............. 252/316; 424/19, 35, 424/341

[56] References Cited

U.S. PATENT DOCUMENTS

| | | | |
|---|---|---|---|
| 3,155,590 | 11/1964 | Miller et al. ................ | 252/316 X |
| 3,173,878 | 3/1965 | Reyes ........................ | 252/316 |
| 3,184,386 | 5/1965 | Stephenson ................ | 424/35 X |
| 3,341,416 | 9/1967 | Anderson et al. ........... | 252/316 X |
| 3,623,997 | 11/1971 | Powell ........................ | 252/316 |
| 4,123,382 | 10/1978 | Morse et al. ............... | 252/316 |

OTHER PUBLICATIONS

Merck Index, Eighth Edition, 1968, p. 951.

*Primary Examiner*—Richard D. Lovering
*Attorney, Agent, or Firm*—Hubbell, Cohen, Stiefel & Gross

[57] ABSTRACT

A process for the preparation of pharmaceutical substance-containing microcapsules by liquid-liquid phase separation is disclosed. In this process, ethyl cellulose having an ethoxy content of about 48 to about 49.5% by weight is used as a wall-forming agent and polyisobutylene is used as a phase separation inducing agent, and both or either one of the ethyl cellulose and polyisobutylene are used in the form of a mixture of two kinds differing in the average molecular weight.

8 Claims, 5 Drawing Figures

PROCESS FOR THE PREPARATION OF PHARMACEUTICAL SUBSTANCE-CONTAINING MICROCAPSULES

BACKGROUND OF THE INVENTION (1) Field of the Invention

The present invention relates to pharmaceutical substance-containing microcapsules and a process for the preparation of the same.

(2) Brief Description of the Prior Art

As the conventional microencapsulation process for microencapsulating a pharmaceutical substance insoluble in cyclohexane, such as aspirin, with ethyl cellulose, a process is known in which butyl rubber or polyethylene is used as a phase separation inducing agent and is dissolved by heating into a cyclohexane solution containing ethyl cellulose, a powder of a pharmaceutical substance is dispersed in the solution and the dispersion is cooled to cause phase separation and form pharmaceutical substance-containing microcapsules (see Japanese Patent Publication No. 528/67 and Japanese Patent Publication No. 11399/69). According to this known process, however, it is impossible to increase the wall thickness beyond a certain level in resulting capsules, and therefore, a sufficient effect of retarding release of the pharmaceutical ingredient cannot be attained.

As an improvement of the above-mentioned conventional process, there has been proposed a process in which microcapsules prepared according to the above-mentioned process are further treated with paraffin to form a double-wall structure (see British Pat. No. 1,117,270). This Process, however, has disadvantages in that the steps for forming microcapsules are complicated and it is very difficult to remove the solvent used sufficiently from the capsule wall. Further, no satisfactory effect of retarding release of the pharmaceutical ingredient can be attained.

As a result of investigations, we previously proposed a process for microencapsulating a pharmaceutical substance with ethyl cellulose by liquid-liquid phase separation, wherein polyisobutylene having an average moleculr weight of 8,700 to 135,000 or its mixture with butyl rubber having an unsaturation degree of 0.7 to 3.0 mole % is used as the phase separation inducing agent (see Japanese Patent Publication No. 30136/75). According to this process, the wall thickness can be adjusted within a range of from a thickness providing a semipermeable membrane wall to a thickness providing an impermeable membrane wall, and therefore, microcapsules having a quick releasing property or a gradual releasing property can optionally be prepared. However, according to this process, in order to retard release of the pharmaceutical ingredient, it is necessary to increase the wall thickness of microcapsules. Increase of the wall thickness of microcapsules naturally results in dilution of the pharmaceutical ingredient as a core. Accordingly, incorporation ratios of an excipient, a disintegrating agent, a binder and a lubricating agent to be used for formation of powders, granules, fine particles, tablets and capsules are drastically limited, and formulation of medicaments becomes very difficult. Further, if the wall thickness is increased, the deviation of the speed of release of the pharmaceutical ingredient becomes large, and in some case, the pharmaceutical ingredient cannot completely be released. Furthermore, when such microcapsules are mixed the other ingredient, the amount of said other component adsorbed in the capsule wall is increased and the quality of the resulting medicine is degraded. It has been found that these disadvantages are involved in the previously proposed process.

BRIEF SUMMARY OF THE INVENTION

An object of the invention is to eliminate the foregoing defects and disadvantages involved in the conventional processes. It was found that in preparing pharmaceutical substance-containing microcapsules by liquid-liquid phase separation, when a mixture of two ethyl celluloses having an ethoxy content of about 48 to about 49.5% by weight, one having a viscosity of about 90 to about 110 cps and the other having viscosity lower by at least about 40 cps than the viscosity of said one ethyl cellulose, is used as the wall-forming agent and polyisobutylene having an average molecular weight of about 8,000 to about 140,000 or a mixture of polyisobutylene having an average molecular weight of about 8,000 to about 12,000 and polysiobutylene having an average molecular weight of about 60,000 to about 140,000 is used as the phase separation inducing agent, or when one ethyl cellulose having an ethoxy content within the above-mentioned range and a viscosity of about 6 to about 110 cps is used singly as the wall-forming agent and said mixture of the two polyisobutylenes is used as the phase separation inducing agent, wall characteristics of the ethyl cellulose film deposited on particles of a pharmaceutical substance can be remarkably improved and the compactness or texture of said film can be freely adjusted to some extent, and therefore, release of the pharmaceutical ingredient from capsules can be controlled without substantially changing the wall thickness.

More specifically, in accordance with the present invention, there is provided a process for the preparation of pharmaceutical substance-containing microcapsules by liquid-liquid phase separation using ethyl cellulose having an ethoxy content of about 48 to about 49.5% by weight as a wall-forming agent and polyisobutylene as a phase separation inducing agent, said process being characterized in that (a) a mixture of ethyl cellulose having a viscosity of about 90 to about 110 cps and ethyl cellulose having a viscosity lower by at least about 40 cps than the viscosity of the first-mentioned ethyl cellulose is used as the ethyl cellulose and polyisobutylene having an average molecular weight of about 8,000 to about 140,000 is used as the polyisobutylene, (b) a mixture of ethyl cellulose having a viscosity of about 90 to about 110 cps and ethyl cellulose having a viscosity lower by at least about 40 cps than the viscosity of the first-mentioned ethyl cellulose is used as the ethyl cellulose and a mixture of polyisobutylene having an average molecular weight of about 8,000 to about 12,000 and polyisobutylene having an average molecular weight of about 60,000 to about 140,000 is used as the polyisobutylene or (c) ethyl cellulose having a viscosity of about 6 to about 110 cps is used as the ethyl cellulose and a mixture of polyisobutylene having an average molecular weight of about 8,000 to about 12,000 and polyisobutylene having an average molecular weight of about 60,000 to about 140,000 is used as the polyisobutylene.

DETAILED DESCRIPTION OF THE PREFERRED EMBODIMENTS

Figure 1:
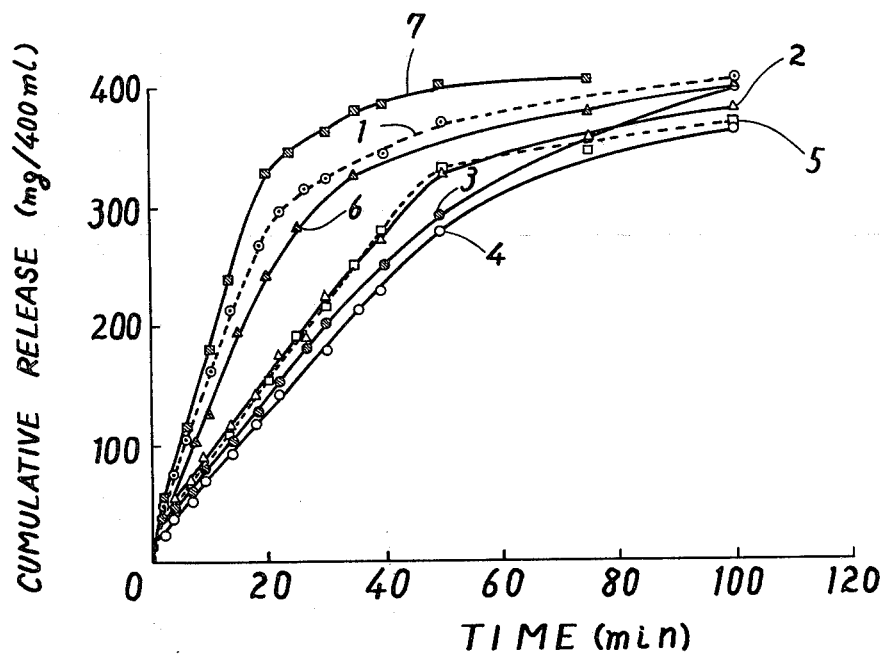
FIGS. 1 to 4 are curves illustrating the change of the amount of vitamin C dissolved out with the lapse of time when vitamin C-containing microcapsules obtained in Experiments 1 to 4 are put into a first fluid for the disintegration test described in the pharmacopeia of Japan, the 9th Edition.

The ethyl cellulose used as the wall-forming agent in the present invention, is ethyl cellulose having an ethoxy content of about 48 to about 49.5% by weight and having a viscosity of about 6 to about 110 cps and a mixture of two ethyl celluloses having an ethoxy content of about 48 to about 49.5% by weight, one having a viscosity of about 90 to about 110 cps and the other having a viscosity lower by at least about 40 cps than the viscosity of said one ethyl cellulose (ethyl cellulose having a viscosity of about 6 to about 110 cps will hereinafter be referred to as "ethyl cellulose" and a mixture of two ethyl celluloses differing in the viscosity will hereinafter be referred to as "ethyl cellulose mixture").

The viscosity of ethyl cellulose used as the wall-forming agent in the present invention is measured at 25° C. with respect to a 5% by weight solution of the ethyl cellulose in a toluene/ethanol mixed solvent (mixing ratio=4/1).

The polyisobutylene used as the phase separation inducing agent in the present invention, is a polyisobutylene having a high degree of saturation and containing unsaturated groups only in the terminal portions of the polymer chain, which has Staudinger's viscosity-average molecular weight of about 8,000 to about 140,000, especially about 10,000 to about 120,000, and a mixture of two polyisobutylenes having a high degree of saturation and containing unsaturated groups only in the terminal portions of the polymer chain, one having a Staudinger's viscosity-average molecular weight of about 8,000 to about 12,000 and the other having a Staudinger's viscosity-average molecular weight of about 60,000 to about 140,000 (polyisobutylene having an average molecular weight of about 8,000 to about 140,000 will hereinafter be referred to as "polyisobutylene" and a mixture of two polyisobutylenes differing in the average molecular weight will hereinafter be referred to as "polyisobutylene mixture").

According to the present invention, release of the pharmaceutical ingredient can be controlled without substantially changing the wall thickness of microcapsules by changing the texture or compactness of the walls of microcapsules. For this purpose, the following combinations of the wall-forming agent and phase separation inducing agent are ordinarily adopted.

(a) Ethyl cellulose mixture and polyisobutylene.
(b) Ethyl cellulose mixture and polyisobutylene mixture.
(c) Ethyl cellulose and polyisobutylene mixture.

These combinations of the wall-forming agent and phase separation inducing agent will now be described in detail.

In case of the combination (a), as the mixing ratio of low viscosity ethyl cellulose to high viscosity ethyl cellulose in the ethyl cellulose mixture as the wall-forming agent is increased, the gradual releasing property is enhanced in the resulting microcapsules. In this case, if the difference of the viscosity is too large (at least 80 cps), the mixing effect becomes insignificant.

In case of the combination (b), as the mixing ratio of high viscosity ethyl cellulose is increased, the gradual releasing property is enhanced, and in case of the combination (c), as the viscosity of ethyl cellulose is high, the gradual releasing property is enhanced.

In case of the combinations (a) and (b), if a mixture of equal amounts of high viscosity and low viscosity ethyl celluloses are used, as the difference of the viscosity is increased beyond 40 cps, the quick releasing property becomes conspicuous in the resulting microcapsules, and when the viscosity difference is about 40 cps, release of the pharmaceutical ingredient is most retarded.

In case of the combination (c) where the polyisobutylene mixture is used as the phase separation inducing agent, when a mixture of equal amounts of high molecular weight and low molecular weight polyisobutylene is used, the gradual releasing property is most conspicuous, and when one polyisobutylene is used in an amount larger than that of the other polyisobutylene, as the mixing ratio of said one polyisobutylene is increased, the quick releasing property is enhanced.

In the ethyl cellulose mixture which is used in the present invenion, the mixing ratio (weight ratio) of ethyl cellulose having a viscosity of about 90 to about 110 cps to ethyl cellulose having a viscosity lower by at least 40 cps than the viscosity of said ethyl cellulose is ordinarily in the range of from about 0.1 to about 10. In the polyisobutylene mixture, the mixing ratio of polyisobutylene having an average molecular weight of about 8,000 to 12,000 to polyisobutylene having an average molecular weight of about 60,000 to about 140,000 is ordinarily in the range of from about 0.1 to about 10.

In case of the combination (a), the mixing ratio of the ethyl cellulose mixture to polyisobutylene is ordinarily in the range of from about 0.05 to about 30, preferably from about 0.1 to about 10 and in case of the combination (b), the mixing ratio of the ethyl cellulose mixture to the polyisobutylene mixture is ordinarily in the range of from about 0.05 to about 30, preferably from about 0.1 to about 10. In case of the combination (c), the mixing ratio of ethyl cellulose to the polyisobutylene mixture is ordinarily in the range of from about 0.05 to about 30, preferably from about 0.1 to about 10.

In the present invention, pharmaceutical substance-containing microcapsules can be prepared according to the conventional procedures. For example, the wall-forming agent and phase separation inducing agent are dissolved in cyclohexane at 75° to 80° C. and a powder of a pharmaceutical substance is dispersed in the so formed hot cyclohexane solution. When the dispersion is gradually cooled, at about 70° C. the concentrated solution of the wall-forming agent is deposited on the surfaces of particles of the pharmaceutical substance and begins to coat the particles in the form of a liquid wall. When the temperature is further lowered to room temperature, release of cyclohexane from the liquid wall takes place and the liquid wall is converted to a wall gelled more or less, and pharmaceutical substance-containing microcapsules are thus formed. It is preferred that ethyl cellulose or the ethyl cellulose mixture as the wall-forming agent be dissolved in cyclohexane at a concentration of about 0.5 to about 10% by weight. It is preferred that polyisobutylene or the polyisobutylene mixture be dissolved in cyclohexane at a concentration of about 0.3 to about 10% by weight.

Any of pharmaceutical substances (medicaments) incompatible or insoluble in the above-mentioned wall-forming agent and phase separation inducing agent and cyclohexane can be used as the pharmaceutical substance to be microencapsulated in the process of the present invention. In order to attain a homogeneous dispersing state at the microencapsulation step and facilitate removal of ethyl cellulose particles free from the pharmaceutical substance, which are formed as by-products, by sieving after the microencapsulation, it is preferred that the particle size of the powdery pharmaceutical substance be in the range of from about 30 to about 1,000μ.

The so formed pharmaceutical substance-containing microcapsules are collected by decantation, centrifugal separation, filtration or the like means, and then, they are washed with cyclohexane and dried.

According to the present invention, a particle size of the pharmaceutical substance-containing microcapsules may be in the range of from about 30μ to about 3,000μ, depending upon the kind of pharmaceutical substances or the purpose of use.

According to the present invention, by using two ethyl celluloses, differing in viscosity as the wall-forming agent and/or using two polyisobutylenes differing in the average molecular weight as the phase separation inducing agent, the film characteristics of the capsule wall can be improved, and the porosity, tortuosity, or density can be adjusted freely to some extent. Further, release of the pharmaceutical ingredient from microcapsules can be controlled without substantially changing the wall thickness in the microcapsules. Still further, the wall thickness can optionally be adjusted by changing the ratio between the pharmaceutical substance and the wall-forming agent. Furthermore, effects of stabilizing the pharmaceutical substance, sustaining the activity of the pharmaceutical substance and improving such factors as taste, smell and stimulus can be sufficiently attained. These are advantages attained according to the present invention.

The present invention will now be described in detail by reference to the following Experiments and Examples that by no means limit the scope of the invention.

EXPERIMENT 1

Into a mixture of a ml of a 3% by weight solution of polyisobutylene having an average molecular weight of 11,000 in cyclohexane and (300-a) ml of a 3% by weight solution of polyisobutylene having an average molecular weight of 90,000 in cyclohexane was incorporated 3 g of ethyl cellulose having an ethoxy content of 49.2% by weight and a viscosity of 100 cps as measured at 25° C. with respect to a 5% by weight solution in a toluene/ethanol mixed solvent (mixing ratio=4/1), and the ethyl cellulose was dissolved at 78° C. Then, 15 g of powdery vitamin C having a particle size of 149 to 210μ was dispersed in the resulting solution, and the dispersion was cooled to room temperature at a rate of 0.5° C./min. The formed microcapsules were recovered by filtration, washed several times with cyclohexane and dried to obtain about 16 g of vitamin C-containing microcapsules.

The so formed microcapsules were put into a first fluid for the disintegration test specified in the pharmacopeia of Japan, the 9th Edition, and the time $t_{50}$ required for 50% of vitamin C to be dissolved out was measured to obtain results shown in Table 1. Further, the change of the amount of vitamin C dissolved out from the microcapsules with the lapse of time was examined to obtain results shown in FIG. 1.

Table 1

| Run No. | Mixing Ratio of Phase Separation Inducing Agent Solutions | | Amount (%) of Vitamin C in Capsules | Dissolution Time $t_{50}$ (minutes) |
|---|---|---|---|---|
| | a (ml) | 300 - a (ml) | | |
| 1 | 300 | 0 | 93.6 | 12.1 |
| 2 | 240 | 60 | 91.8 | 28.0 |
| 3 | 180 | 120 | 91.3 | 30.0 |
| 4 | 150 | 150 | 88.8 | 36.3 |
| 5 | 120 | 180 | 90.4 | 28.5 |
| 6 | 90 | 210 | 88.0 | 16.5 |
| 7 | 0 | 300 | 94.1 | 11.9 |

Then, 50 ml of the vitamin C-containing microcapsules obtained in Run No. 5 were mixed with 25 mg of bisbenzamine, 100 mg of lactose and 1 mg of magnesium stearate, and a tablet having a hardness of 8 Kg and a weight of 176 mg was prepared from this mixture according to the direct powder compression method. For comparison, a tablet was prepared in the same manner as described above except that 50 mg of vitamin C having a particle size of 149 to 210μ was used instead of the above-mentioned microcapsules.

These tablets were stored under conditions of a temperature of 40° C. and a relative humidity of 75% for 7 days. The comparative tablet was discolored to yellowish brown and the color difference value ΔE was about 51. In contrast, in the table prepared by using the vitamin C-containing microcapsules, no discoloration was observed and the color difference value ΔE was 0.3.

EXPERIMENT 2

In a liquid mixture of 150 ml of a 3% by weight solution of polyisobutylene having an average molecular weight of 10,000 in cyclohexane and 150 ml of a 3% by weight solution of polyisobutylene having an average molecular weight of 100,000 in cyclohexane was dissolved 3 g of a mixture of ethyl celluloses (having an ethoxy content of 48.5%) shown in Table 2 at a temperature of 78° C. Then, 15 g of vitamin C having a particle size of 149 to 210μ was dispersed in the solution and about 16 g of vitamin C-containing microcapsules were prepared in the same manner as described in Experiment 1.

Figure 2:
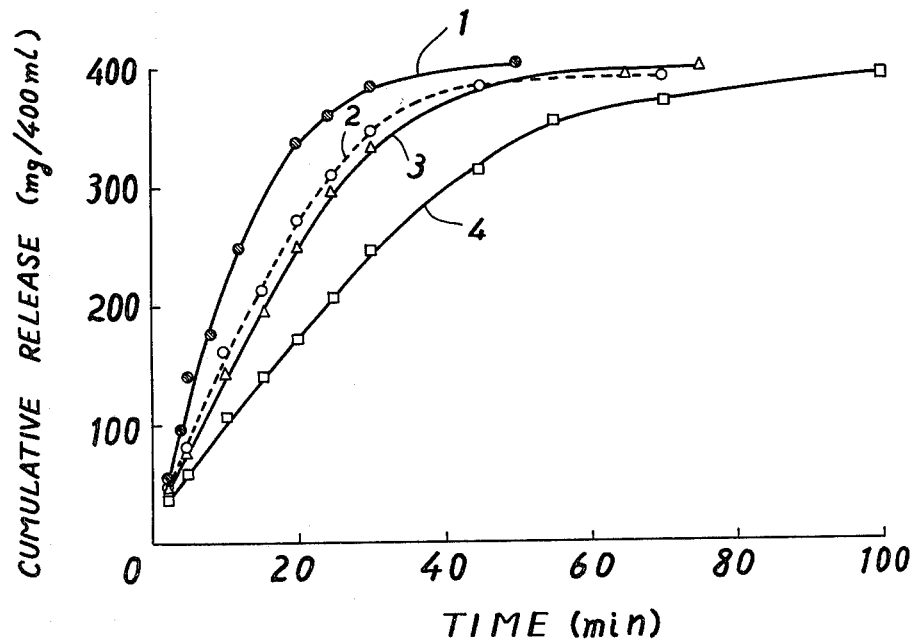

The so prepared microcapsules were put into a first fluid for the disintegration test specified in the said Pharmacopeia of Japan, and the time $t_{50}$ required for 50% of vitamin C to be dissolved out from the capsules was measured to obtain results shown in Table 2. Further, the change of the amount of vitamin C dissolved out from the capsules was examined to obtain results shown in FIG. 2.

Table 2

| Run No. | Mixing Ratio of Ethyl Cellulose | | Amount (%) of Vitamin C in Capsules | Dissolution Time $t_{50}$ (minutes) |
|---|---|---|---|---|
| | 100 cps (g) | 45 cps (g) | | |
| 1 | 0.9 | 2.1 | 88.7 | 9.5 |
| 2 | 1.5 | 1.5 | 89.2 | 14.0 |
| 3 | 2.1 | 0.9 | 89.9 | 15.8 |
| 4 | 2.7 | 0.3 | 88.8 | 24.0 |

EXPERIMENT 3

In 300 ml of a 3% by weight solution of polyisobutylene having an average molecular weight of 110,000 in cyclohexane was dissolved 3 g of an ethyl cellulose mixture shown in Table 3 (mixture comprising equal amounts of low viscosity and high viscosity ethyl celluloses having an ethoxy content of 48.5%) at a temperature of 78° C. Then, 15 g of vitamin C having a particle size of 149 to 210μ was dispersed in the solution, and about 16 g of vitamin C-containing microcapsules were prepared from the dispersion in the same manner as described in Experiment 1.

Figure 3:
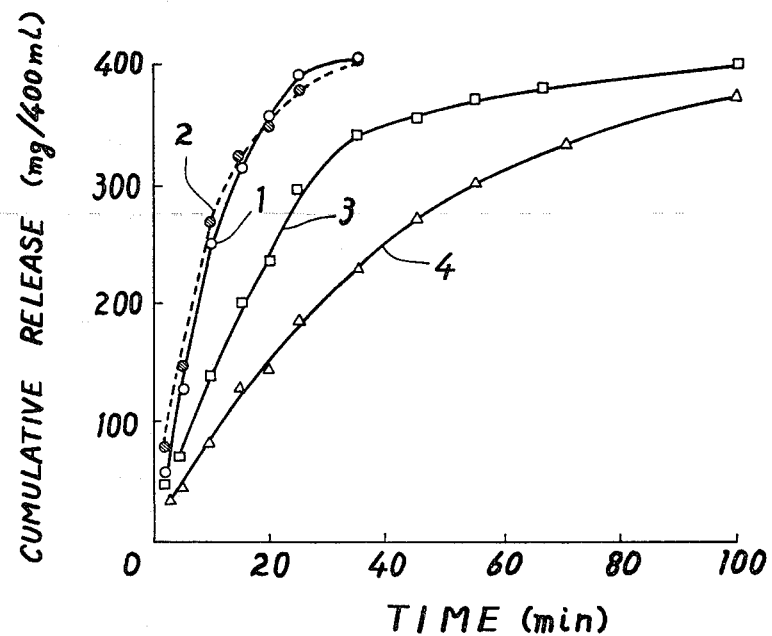

The so prepared microcapsules were put into a first fluid for the disintegration test specified in the said Pharmacopeia of Japan, and the time $t_{50}$ required for 50% of vitamin C to be dissolved out from the capsules was measured to obtain results shown in Table 3. Further, the change of the amount of vitamin C dissolved out from the capsules with the lapse of time was examined to obtain results shown in FIG. 3.

Table 3

| Run No. | Viscosities (cps) of Ethyl Celluloses | | Amount (%) of Vitamin C in Capsules | Dissolution Time $t_{50}$ (minutes) |
|---|---|---|---|---|
| | High Viscosity Ethyl Cellulose | Low Viscosity Ethyl Cellulose | | |
| 1 | 100 | 7 | 94.6 | 8.2 |
| 2 | 100 | 10 | 93.3 | 7.2 |
| 3 | 100 | 20 | 95.0 | 16.0 |
| 4 | 100 | 45 | 94.1 | 29.5 |

EXPERIMENT 4

In 300 ml of a 3% by weight solution of polyisobutylene having an average molecular weight of 90,000 in cyclohexane was dissolved at 78° C. 3 g of a mixture of ethyl celluloses (having an ethoxy content of 48.5%) shown in Table 4. Then, 15 g of vitamin C having a particle size of 149 to 210μ was dispersed in the solution, and 15.5 g of vitamin C-containing microcapsules were prepared in the same manner as described in Experiment 1.

Figure 4:
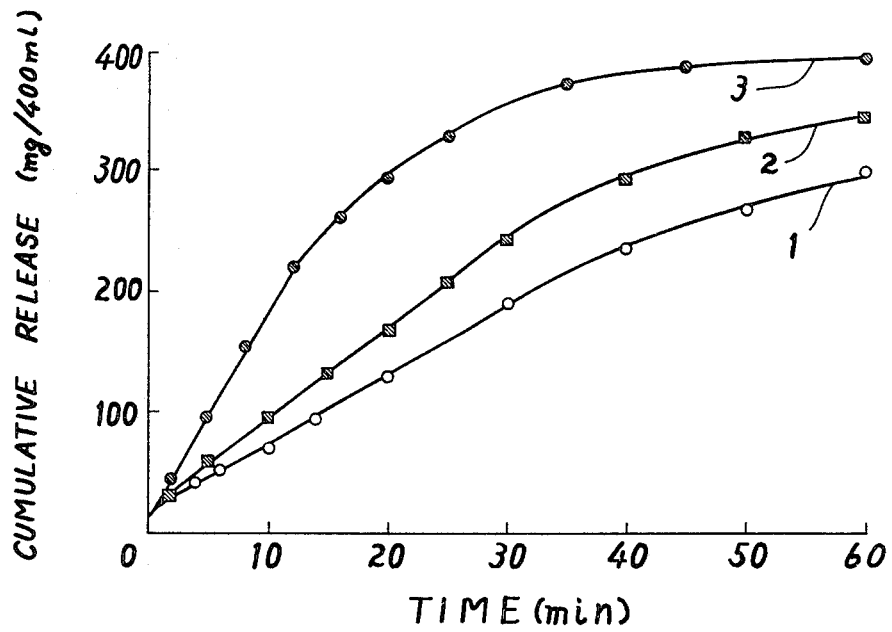

The so prepared microcapsules were put into a first fluid for the disintegration test specified in the said Pharmacopeia of Japan, and the time $t_{50}$ required for 50% of vitamin C to be dissolved out from the capsules was measured to obtain results shown in Table 4. Further, the change of the amount of vitamin C dissolved out from the capsules with the lapse of time was examined to obtain results shown in FIG. 4.

Table 4

| Run No. | Mixing Ratio of Ethyl Celluloses | | Amount (%) of Vitamin C in Capsules | Dissolution Time $t_{50}$ (minutes) |
|---|---|---|---|---|
| | 95 cps (g) | 45 cps (g) | | |
| 1 | 0.6 | 2.4 | 88.4 | 32 |
| 2 | 1.5 | 1.5 | 88.1 | 24 |
| 3 | 2.4 | 0.6 | 90.4 | 11 |

Experiment 5

In a liquid mixture comprising 150 ml of a 3% by weight solution of polyisobutylene having an average molecular weight of 90,000 in cyclohexane and 150 ml of a 3% by weight solution of polyisobutylene having an average molecular weight of 10,000 in cyclohexane was dissolved at 78° C. 3 g of ethyl cellulose having an ethoxy content of 48.5% and a viscosity shown in Table 5. Then, 15 g of trimethoquinol hydrochloride having a particle size of 149 to 210μ was dispersed in the solution and about 16 g of trimethoquinol hydrochloride-containing microcapsules were prepared in the same manner as described in Experiment 1.

Figure 5:
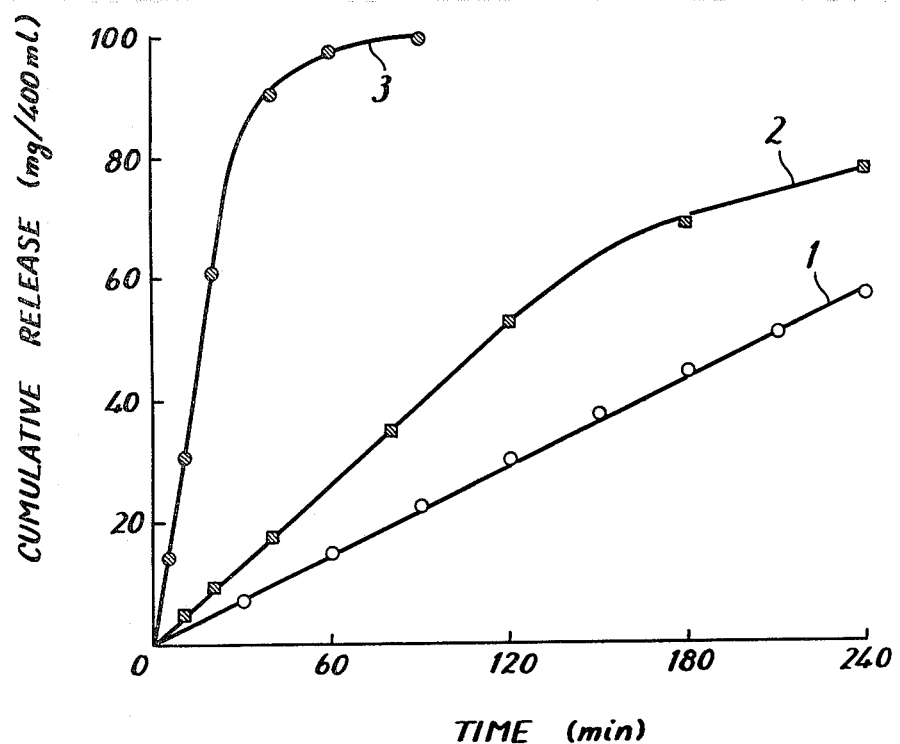
FIG. 5 is a curve illustrating the change of the amount of trimethoquinol hydrochloride dissolved out with the lapse of time when trimethoquinol hydrochloride-containing microcapsules obtained in Experiment 5 are similarly subjected to the dissolution test.

The so prepared microcapsules were put into a first solution for the disintegration test specified in the 9th Revised Japanese Pharmacopeia, and the time $t_{50}$ required for 50% of trimethoquinol hydrochloride to be dissolved out from the capsules was measured to obtain results shown in Table 5. Further, the change of the amount of trimethoquinol hydrochloride dissolved out from the microcapsules with the lapse of time was examined to obtain results shown in FIG. 5.

Table 5

| Run No. | Viscosity (cps) of Ethyl Cellulose | Amount (%) of Trimethoquinol Hydrochloride in Capsules | Dissolution Time $t_{50}$ (minutes) |
|---|---|---|---|
| 1 | 90 | 87.6 | 210 |
| 2 | 48 | 82.8 | 115 |
| 3 | 10 | 82.1 | 17 |

EXAMPLE 1

To 300 ml of a 3% by weight solution of polyisobutylene having an average molecular weight of 126,000 in cyclohexane was added a mixture of 1.0 g of ethyl cellolose having a viscosity of 100 cps as measured at 25° C. with respect to a 5% by weight solution in a mixed solvent of toluene/ethanol (mixing ratio=4/1) and an ethoxy content of 48.5% by weight and 2.0 g of ethyl cellulose having a viscosity of 45 cps as measured under the above-mentioned conditions and an ethoxy content of 49.0% by weight, and the resulting mixture was heated to about 78° C. under agitation at 400 rpm. Then, 15 g of trimethoquinol hydrochloride having a particle size of 149 to 297μ was incorporated and dispersed in the resulting solution, and the dispersion was cooled to room temperature at a rate of 0.5° C./min. The formed microcapsules were recovered by filtration, washed several times with cyclohexane and dried to obtain 16.3 g of trimethoquinol hydrochloride-containing microcapsules.

The microcapsules contained 89.1% of trimethoquinol hydrochloride.

When the microcapsules were put into a first fluid for the disintegration test specified in the said Pharmacopeia of Japan, it was found that the time required for 50% of trimethoquinol hydrochloride to be dissolved out from the microcapsules was 165 minutes.

EXAMPLE 2

In a liquid mixture comprising 120 ml of a 3% by weight solution of polyisobutylene having an average molecular weight of 11,000 in cyclohexane and 180 ml of a 3% by weight solution of polyisobutylene having an average molecular weight of 90,000 in cyclohexane was incorporated 3 g of ethyl cellulose having a viscosity of 100 cps as measured at 25° C. with respect to a 5% by weight solution in a toluene/ethanol mixed solvent and an ethoxy content of 49.2% by weight. The mixture was heated at 78° C. under agitation at 400 rpm, and 30 g of vitamin C having a particle size of 149 to 210μ was dispersed in the resulting solution. The formed dispersion was treated in the same manner as described in Example 1 to obtain 29.1 g of vitamin C-containing microcapsules.

The vitamin C content in the prepared microcapsules was 92.8%.

When the microcapsules were put into a first fluid for the disintegration test specified in the said Pharmacopeia of Japan, it was found that the time required for 50% of vitamin C to be dissolved out was 9.7 minutes.

EXAMPLE 3

In a liquid mixture comprising 120 ml of a 3% by weight solution of polyisobutylene having an average molecular weight of 10,000 in cyclohexane and 180 ml of a 3% by weight solution of polyisobutylene having an average molecular weight of 90,000 in cyclohexane was incorporated 7.5 g of ethyl cellulose having a viscosity of 100 cps as measured at 25° C. with respect to a 5% by weight solution of a toluene/ethanol mixed solvent (mixing ratio=4/1) and an ethoxy content of 48.3% by weight. The mixture was heated at 78° C. under agitation at 400 rpm and 15 g of triprolidine hydrochloride having a particle size of 297 to 500μ was dispersed in the resulting solution. The dispersion was treated in the same manner as described in Example 1 to obtain 17.1 g of triprolidine hydrochloride-containing microcapsules.

The triprolidine hydrochloride content in the prepared microcapsules was 85.6%. When the prepared microcapsules were put into a first fluid for the disintegration test specified in the said Pharmacopeia of Japan, it was found that the time required for 50% of triprolidine hydrochloride to be dissolved out was 42 minutes.

EXAMPLE 4

To a liquid mixture comprising 150 ml of a 3% by weight solution of polyisobutylene having an average molecular weight of 100,000 in cyclohexane and 150 ml of a 3% by weight solution of polyisobutylene having an average molecular weight of 10,000 in cyclohexane was added a mixture comprising 1.5 g of ethyl cellulose having a viscosity of 100 cps as measured at 25° C. with respect to a 5% by weight solution in a toluene/ethanol mixed solvent (mixing ratio=4/1) and an ethoxy content of 48.5% and 1.5 g of ethyl cellulose having a viscosity of 45 cps as measured under the above-mentioned conditions and an ethoxy content of 48.5%. The mixture was heated at about 78° C. under agitation at 400 rpm, and 15 g of trimethoquinol hydrochloride having a particle size of 149 to 210μ was dispersed in the resulting solution. Then, the dispersion was cooled to room temperature at a rate of 0.5° C./min. The resulting microcapsules were recovered by filtration, washed several times with cyclohexane and dried to obtain 16.0 g of trimethoquinol hydrochloride-containing microcapsules.

The trimethoquinol hydrochloride content is the formed microcapsules was 86.6%.

When the microcapsules were put into a first fluid for the disintegration test specified in the said Pharmacopeia of Japan, it was found that the time required for 50% of trimethoquinol hydrochloride to be dissolved out was 180 minutes.

Referential Experiment

Microcapsules were prepared according to our previously proposed process disclosed in Japanese Patent Publication No. 30136/75 and also to the process of the present invention, and permeability coefficient (P) of both microcapsules were measured and they were compared with each other with respect to the permeability.

(1) Microcapsules according to the process of Japanese Patent Publication No. 30136/75 were prepared in the following manner.

To 200 ml of a 3% by weight solution of polyisobutylene having an average molecular weight of 81,000 to 99,000 in cyclohexane was added 4 g of ethyl cellulose, and the mixture was heated at 80° C. to dissolve the ethyl cellulose. Then, 32 g (sample A) or 40 g (sample B) of trimethylquinol hydrochloride having a particle size as described in Table 6 was dispersed in the resulting solution. Then, the dispersion was cooled to room temperature at a rate of 1° C./min. The formed precipitate was recovered by filtration, washed several times with cyclohexane and dried to obtain trimethoquinol hydrochloride-containing microcapsules.

(2) Microcapsules (containing vitamin C as the pharmaceutical ingredient) prepared in Run No. 4 of Experiment 1 were used as the microcapsules of the present invention (sample C). Further, microcapsules containing trimethoquinol hydrochloride as the pharmaceutical ingredient (sample D) were prepared in the same manner as in Run No. 4 of Experiment 1 and uses as the microcapsules of the present invention.

These microcapsules (samples A to D) were subjected to the dissolution test in the same manner as described in Experiment 1 and the permeability coefficient was calculated with respect to each sample to obtain results shown in Table 6.

Table 6

| | Microcapsules of Japanese Patent Publication No. 30136/75 | | Microcapsules of the Invention | |
|---|---|---|---|---|
| | Sample A | Sample B | Sample C* | Sample D |
| Core Material Diameter (mm) | 0.01875 | 0.01875 | 0.00898 | 0.00898 |
| Core Material Content (%) | 86.3 | 90.0 | 88.8 | 87.6 |
| Core Material Solubility (mg/ml) | 25.9 | 25.9 | 350 | 25.9 |
| Amount (mg) of Core Material in Microcapsules Used for Dissolution Test | 431.5 | 450 | 400 | 400 |
| Slope (mg/min) of Dissolution Curve | 1.04 | 1.98 | 5.63 | 0.96 |
| Permeability Coefficient P(cm$^2$/sec) | $1.00 \times 10^{-8}$ | $1.40 \times 10^{-8}$ | $1.24 \times 10^{-9}$ | $2.11 \times 10^{-9}$ |

*The pharmaceutical ingredient in sample C was vitamin C, and in other samples, the pharmaceutical ingredient was trimethoquinol hydrocloride.

The permeability coefficient (P) is a value inherent of a membrane or film, which indicates the easiness or difficulty of permeation through the membrane or film. This is a function of not only the diffusion of core material molecules but also the porosity and tortuosity of the membrane or film. A larger value of the permeability coefficient (P) means that the membrane or film, i.e., the wall, is more porous and the passage for molecules of the pharmaceutical ingredient as the core material is shorter. Therefore, a large value of the permeability coefficient (P) indicates that permeation of the core material is easier.

As will be apparent from the results shown in Table 6, the value (P) is $1 \times 10^{-9}$ to $2 \times 10^{-9}$ in vitamin C- and trimethoquinol hydrochloride-containing microcapsules prepared according to the present invention (samples C and D), but in trimethoquinol hydrochloride-containing microcapsules according to the process of Japanese Patent Publication No. 30136/75 (samples A and B), the value (P) is $10^{-8}$. Namely, the value (P) of microcapsules according to the process of Japanese Patent Publication No. 30136/75 is about 10 times as high as the value (P) of microcapsules according to the present invention. In other words, the microcapsules according to Japanese Patent Publication No. 30136/75 have a structure in which passage of core material molecules through the wall is about 10 times as easy as in the microcapsules according to the present invention. Thus, it has been confirmed that the present invention is superior to the invention of Japanese Patent Publication No. 30136/75.

What we claim is:

1. A process for the preparation of microcapsules containing a pharmaceutical substance which comprises dissolving
    a mixture of a first ethyl cellulose having a viscosity of about 90 to 110 cps and a second ethyl cellulose having a viscosity lower by at least about 40 cps than the viscosity of the first ethyl cellulose, the weight ratio of said first ethyl cellulose to said second ethyl cellulose being in the range of from about 0.1 to about 10;
    and polyisobutylene having an average molecular weight of about 8,000 to about 140,000;
    in a solvent to form a solution thereof, said ethyl cellulose mixture having an ethoxy content of about 48 to about 49.5% by weight.
    dispersing a powder of a pharmaceutical substance in said solution to form a dispersion;
    cooling said dispersion; and
    separating the thereby formed microcapsules containing said pharmaceutical substance from said dispersion.

2. A process as claimed in claim 1, wherein the weight ratio of the ethyl cellulose mixture to polyisobutylene is in the range of from about 0.05 to 30.

3. A process as claimed in claim 2, wherein the weight ratio is in the range of from 0.1 to about 10.

4. A process for the preparation of microcapsules containing a pharmaceutical substance which comprises dissolving
    a mixture of ethyl cellulose having a viscosity of about 90 to 110 cps and ethyl cellulose having a viscosity lower by at least about 40 cps than the viscosity of the first-mentioned ethyl cellulose and a mixture of polyisobutylene having an average molecular weight of about 8,000 to about 12,000 and polyisobutylene having an average molecular weight of about 60,000 to about 140,000;
    the weight ratio of polyisobutylene having an average molecular weight of about 8,000 to 12,000 to polyisobutylene having an average molecular weight of about 60,000 to about 140,000 being in the range of from about 0.1 to about 10;
    in a solvent to form a solution thereof, said ethyl cellulose mixture having an ethoxy content of about 48 to about 49.5% by weight;
    dispersing a powder of a pharmaceutical substance in said solution to form a dispersion;
    cooling said dispersion; and
    separating the thereby formed microcapsules containing said pharmaceutical substance from said dispersion.

5. A process as claimed in claim 4, wherein the weight ratio of the ethyl cellulose mixture to the polyisobutylene mixture is in the range of from about 0.05 to about 30.

6. A process as claimed in claim 5, wherein the weight ratio is in the range of from about 0.1 to about 10.

7. A process for the preparation of microcapsules containing a pharmaceutical substance which comprises dissolving
    ethyl cellulose having a viscosity of about 6 to about 110 cps and a mixture of polyisobutylene having an average molecular weight of about 8,000 to about 12,000 and polyisobutylene having an average molecular weight of about 60,000 to about 140,000;
    the weight ratio of ethyl cellulose to the polyisobutylene mixture being in the range of from about 0.05 to about 30;
    in a solvent to form a solution thereof, said ethyl cellulose mixture having an ethoxy content of about 48 to about 49.5% by weight.
    dispersing a powder of a pharmaceutical substance in said solution to form a dispersion;
    cooling said dispersion; and
    separating the thereby formed microcapsules containing said pharmaceutical substance from said dispersion.

8. A process as claimed in claim 7, wherein the weight ratio is in the range of from about 0.1 to about 10.

* * * * *

UNITED STATES PATENT OFFICE
CERTIFICATE OF CORRECTION

Patent No. 4,218,333             Dated Aug. 19, 1980

Inventor(s)   Masayoshi Samejima et al.

It is certified that error appears in the above-identified patent and that said Letters Patent are hereby corrected as shown below:

Column 1, line 67:  after "mixed" insert --with--.

Column 4, line 18:  "polyisobutylene" should read --polyisobutylenes--.

Column 6, line 16:  "ml" should read --mg--.

Column 6, line 57:  "Cellulose" should read --Celluloses--.

Column 10, line 4:  "is" should read --in--.

Column 11, line 49:  the period (.) should be a semi-colon (;).

Signed and Sealed this

Thirtieth Day of August 1983

[SEAL]

Attest:

GERALD J. MOSSINGHOFF

Attesting Officer     Commissioner of Patents and Trademarks